United States Patent
Pham Duc

(10) Patent No.: US 7,554,002 B2
(45) Date of Patent: Jun. 30, 2009

(54) METHOD FOR COLD SUPPLY TO THE LOW-TEMPERATURE SEPARATION STAGE OF AN OLEFIN PLANT

(75) Inventor: Tuat Pham Duc, Penzberg (DE)

(73) Assignee: Linde Aktiengesellschaft, Wiesbaden (DE)

( * ) Notice: Subject to any disclaimer, the term of this patent is extended or adjusted under 35 U.S.C. 154(b) by 170 days.

(21) Appl. No.: 11/703,213

(22) Filed: Feb. 7, 2007

(65) Prior Publication Data
US 2007/0199865 A1      Aug. 30, 2007

(30) Foreign Application Priority Data
Feb. 8, 2006    (DE) .................. 10 2006 005 822

(51) Int. Cl.
*C07C 7/00*     (2006.01)

(52) U.S. Cl. .................. 585/802; 585/800; 585/809
(58) Field of Classification Search .................. 585/800, 585/802, 809
See application file for complete search history.

(56) References Cited

U.S. PATENT DOCUMENTS 5,453,559 A * 9/1995 Phillips et al. .............. 585/809

* cited by examiner

*Primary Examiner*—Jafar Parsa
(74) *Attorney, Agent, or Firm*—Millen, White, Zelano & Branigan, P.C.

(57) ABSTRACT

A method is described for refrigerant supply of a low-temperature separation stage in a plant for producing olefins from hydrocarbon-containing feed (olefin plant). During the separation sequence beginning with a front end deethanizer (3) downstream of raw gas compressor (1), precooler and dryer (2), first separation is performed into an olefin fraction having at most two carbon atoms and an olefin fraction having at least three carbon atoms. The fraction having at least three carbon atoms is conducted to the further separation sequence for longer-chain olefins (4). The fraction having at most two carbon atoms is conducted via a catalytic hydrogenation stage (5) connected in between to the low-temperature separation stage (6) which comprises three condensation stages in the temperature range from −50° C. to −100° C. From the low-temperature separation stage, gaseous hydrogen (9) and methane (10) are drawn off, while the olefins having at most two carbon atoms are conducted to a further fractionation stage (7). The refrigeration power for the low-temperature separation stage is provided by the vaporization via heat exchangers of a portion of the liquid ethylene fraction (8) resulting in the front end deethanizer. The vaporized ethylene fraction is recirculated to the raw gas compressor (11).

9 Claims, 2 Drawing Sheets

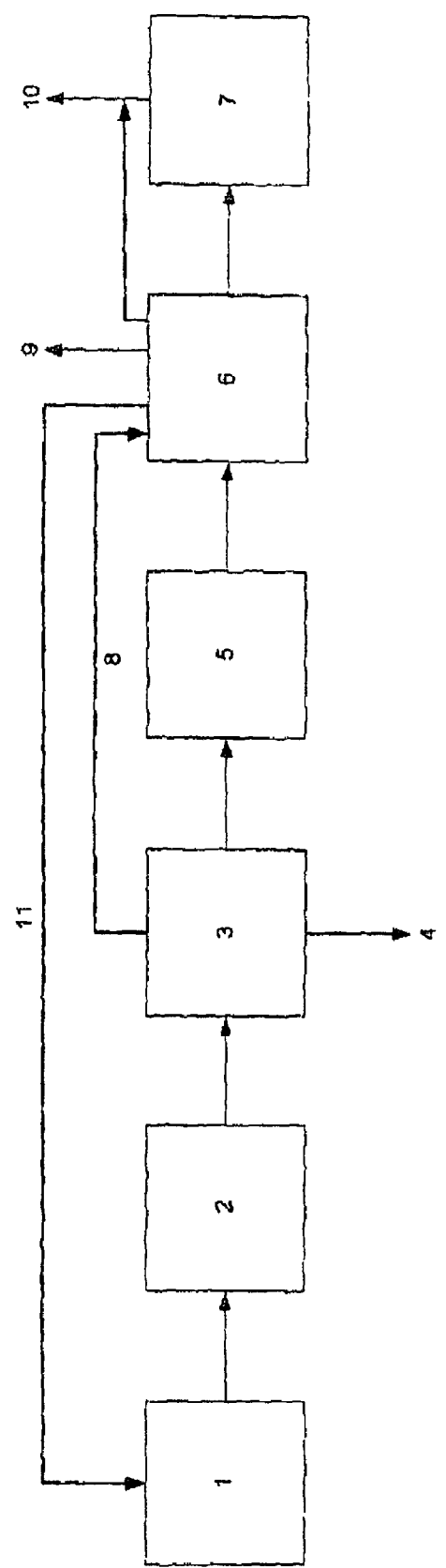

METHOD FOR COLD SUPPLY TO THE LOW-TEMPERATURE SEPARATION STAGE OF AN OLEFIN PLANT

The invention relates to a method for the low-temperature supply of a low-temperature separation stage of olefins using a refrigerant in a plant for olefin production from hydrocarbon-containing feed (olefin plant), with the low-temperature separation stage comprising three condensation stages from −50° C. to −100° C. and being connected downstream of a fractionation stage which separates olefins having at most two carbon atoms from olefins having at least three carbon atoms (front end deethanizer).

Olefins can be produced from longer-chain hydrocarbons, for example, by thermal cracking in a cracking furnace (steam cracker). The gas resulting after the cracking process (raw gas) is separated in a plurality of fractionation stages into olefins having differing numbers of carbon atoms. According to the prior art, methane is separated from olefins having two carbon atoms in a low-temperature separation stage. The low-temperature separation proceeds in three condensation stages, operating at successively lower temperatures in the range from −50° C. to −100° C. In each of the three stages, gaseous hydrogen and methane are separated from the hydrocarbon condensate containing, e.g., ethylene, ethane and methane. Generally, upstream of the low-temperature separation stage is connected a fractionation stage which separates olefins having at most two carbon atoms from olefins having at least three carbon atoms (front end deethanizer). According to the prior art, the refrigeration power for the three condensation stages over the temperature range from −50° C. to −100° C. is generated by a refrigeration cycle in which vaporized ethylene is used as refrigerant which is generated from the ethylene gas stream produced by the olefin plant by corresponding compressor cycles including compressor, turbine, heat exchanger, separator and outlet vessel. See, e.g., H. Zimmermann, R. Walzl, "Ethylene" from Ullmanns' Encyclopedia of Industrial Chemistry, Wiley-VCH, Weinheim, Germany, 2002. The required compressor cycle for ethylene refrigerant generation in this case increases the capital costs, as also the operating risk, of the olefin plant.

SUMMARY OF THE INVENTION

An object of the present invention is to design a method of the type described at the outset in such a manner that the cold supply to the low-temperature separation stage of the olefin plant is reliably ensured in an economical manner.

Upon further study of the specification and appended claims, further objects, aspects and advantages of this invention will become apparent to those skilled in the art.

These objects can be achieved with regard to the method according to the invention by the means that, as refrigerant, a portion of the liquid olefin fraction having two carbon atoms is taken off from the front end deethanizer.

The capital costs of compressor cycles for providing the refrigeration power for the low-temperature separation stage are a not insignificant portion of the capital costs of an olefin plant. In addition, owing to the compressor cycle, the risk of the operating procedure increases and thus is a risk for the availability of the raw gas separation sequence.

The basic concept of the invention is to omit the compressor cycle for ethylene refrigerant generation and to use as refrigerant a portion of the liquid olefin fraction having two carbon atoms from the front end deethanizer.

According to a particularly preferred embodiment of the invention, a portion of the liquid ethylene fraction from the front end deethanizer is used as refrigerant for the three condensation stages of the low-temperature separation stage. Advantageously, the liquid ethylene fraction taken off is conducted via the heat exchangers to the condensation stages and vaporized, as a result of which the desired refrigeration power is generated. The vaporized ethylene is recirculated according to the invention to the raw gas compression stage of the olefin plant.

A development of the inventive concept provides connecting a catalytic hydrogenation stage between the front end deethanizer and the low-temperature separation stage.

By means of the invention, in particular the necessary refrigeration power is successfully provided for the low-temperature separation stage of the olefin plant. At the same time, the capital costs and the risks of the operational procedure are minimized by the omission of a compressor cycle including compressor, turbine, heat exchanger, separator and outlet vessel.

Hereinafter the invention is to be described in more detail on the basis of a comparison between the prior art and an embodiment of the invention shown diagrammatically in FIG. 2.

The entire disclosures of all applications, patents and publications, cited above and below, are hereby incorporated by reference.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein:

FIG. 2 shows a flow chart of an olefin plant according to an embodiment of the invention having a front end deethanizer and subsequent catalytic hydrogenation stage, low-temperature separation stage and cold supply by a portion of the liquid ethylene fraction of the deethanizer.

Figure 1:
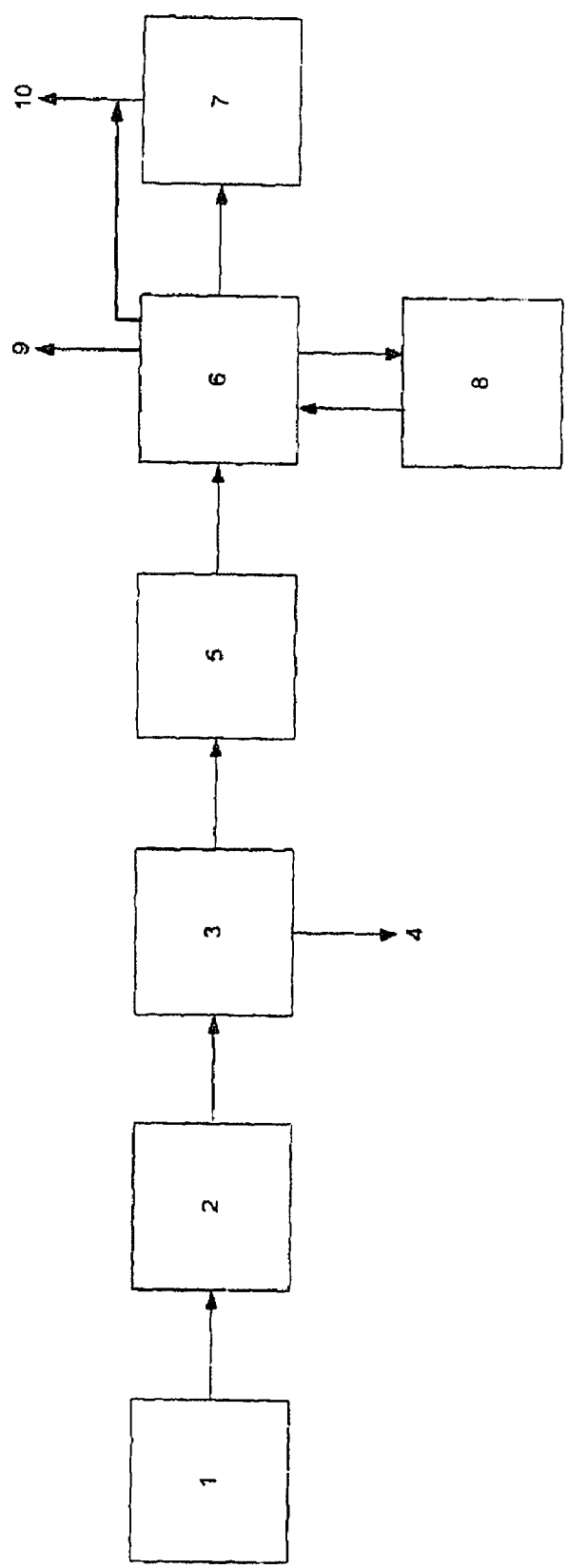
FIG. 1 shows a flow chart of a prior art olefin plant having a front end deethanizer, low-temperature separation stage and cold supply.

The flow chart shown in FIG. 1 exhibits a part of the separation sequence of an olefin plant of the prior art. Downstream of the raw gas compressor (1), the precooler and dryer (2), the raw gas is conducted into the front end deethanizer (3) where the raw gas is separated into a fraction having at most two carbon atoms and a fraction having at least three carbon atoms, with the fraction having at least three carbon atoms being conducted to the further separation sequence of the longer-chain olefins (4). The olefin fraction having at most two carbon atoms is conducted via a catalytic hydrogenation stage (5) to the low-temperature separation stage (6). In the low-temperature separation stage, gaseous hydrogen (9) and methane (10) are drawn off. Thus, in each of the three stages, gaseous hydrogen and methane are separated from the hydrocarbon condensate containing, e.g., ethylene, ethane and methane. From the low-temperature separation stage, the olefins pass to a further fractionation stage (7), a demethanizer, in which methane (10) is separated from olefins having two carbon atoms. The hydrocarbons containing two carbon atoms, mainly ethylene, are removed from fractionation stage (7). The product ethylene from fractionation stage (7) can then be sent to a high-pressure splitter (not shown) wherein ethane is separated from product ethylene. The refrigeration power for the three condensation stages in the temperature range from −50° C. to −100° C. of the low-temperature separation stage (6) is provided via a separate compressor cycle (8).

FIG. 2 shows the flow chart of one embodiment of the invention. Downstream of raw gas compressor (1), precooler and dryer (2), the raw gas is conducted into the front end deethanizer (3). The raw gas delivered to the deethanizer can contain, e.g., hydrogen, methane, ethylene, ethane, $C_{3+}$ hydrocarbons, and other minor components such as CO and $CO_2$. Thus, for example, the raw gas may contain 10-20 mol. % hydrogen, 20-35 mol. % methane, 25-40 mol. % ethylene, 4-8 mol. % ethane, 15-25 $C_{3+}$ hydrocarbons, and 0.5-2.0 mol. %.

In front end deethanizer (3), the raw gas is separated into a fraction having at most two carbon atoms and a fraction having at least three carbon atoms. The fraction having at least three carbon atoms is fed to the further separation sequence for longer-chain olefins (4), while the fraction having at most two carbon atoms is conducted via a catalytic hydrogenation stage (5) to the low-temperature separation stage (6) from where the raw gas is passed on to a fractionation stage (7) (a demethanizer) which separates methane (10) from olefins having two carbon atoms. The hydrocarbons containing two carbon atoms, mainly ethylene, are removed from fractionation stage (7). The product ethylene from fractionation stage (7) can then be sent to a high-pressure splitter (not shown) wherein ethane is separated from product ethylene. From the low-temperature separation stage, gaseous hydrogen (9) and methane (10) are discharged. Thus, for example, in each of the three condensation stages, gaseous hydrogen and methane can be separated from the hydrocarbon condensate containing, e.g., ethylene, ethane and methane. The refrigeration power for the three condensation stages of the low-temperature separation stage is supplied by vaporizing a liquid ethylene fraction (8) from the front end deethanizer (3) via heat exchangers. The vaporized ethylene fraction (11) is recycled back to the raw gas compressor (1).

The entire disclosures of all applications, patents and publications, cited herein and of corresponding German application No. 102006005822.4, filed Feb. 8, 2006, are incorporated by reference herein.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for producing olefins from hydrocarbon-containing feed using a refrigerant and a low-temperature separation stage, said method comprising:
   introducing a hydrocarbon feed containing olefins into a fractionation stage which is a front end deethanizer which separates the hydrocarbon feed into a first olefin stream containing olefins having at most two carbon atoms, and a second olefin stream containing olefins having at least three carbon atoms; and
   introducing at least a portion of said first olefin stream into a low-temperature separation stage comprising three condensation stages, operating at temperatures of −50° C. to −100° C., said low-temperature separation stage being connected downstream of said front end deethanizer, wherein the refrigerant used in said three condensation stages consists essentially of a liquid olefin fraction having two carbon atoms removed from said front end deethanizer, and wherein said method omits a compressor cycle for ethylene refrigerant for said condensation stages.

2. A method according to claim 1, wherein said liquid olefin fraction having two carbon atoms is vaporized via countercurrent flow heat exchangers in said condensation stages.

3. A method according to claim 2, wherein said olefin fraction having two carbon atoms which is vaporized in the countercurrent flow heat exchangers is recirculated to a compressor stage upstream of said front end deethanizer.

4. A method according to claim 1, further comprising a catalytic hydrogenation stage connected between said front end deethanizer and said low-temperature separation stage.

5. A method according to claim 2, further comprising a catalytic hydrogenation stage connected between said front end deethanizer and said low-temperature separation stage.

6. A method according to claim 3, further comprising a catalytic hydrogenation stage connected between said front end deethanizer and said low-temperature separation stage.

7. A method for producing olefins from hydrocarbon-containing feed using a refrigerant and a low-temperature separation stage, said method comprising:
   compressing a hydrocarbon feed containing olefins a gas compressor (1), introducing resultant compressed hydrocarbon feed in a precooler and dryer (2), and introducing the pre-cooled, compressed hydrocarbon feed into a front end deethanizer (3) which separates the hydrocarbon feed into a first olefin stream containing olefins having at most two carbon atoms, and a second olefin stream containing olefins having at least three carbon atoms;
   introducing a portion of said first olefin stream containing olefins having at most two carbon atoms into a catalytic hydrogenation stage (5);
   introducing resultant effluent from said catalytic hydrogenation stage (5) to a low-temperature separation stage (6) comprising three condensation stages operating at temperatures of −50° C. to −100° C., wherein the refrigerant used in said low-temperature separation stage consists essentially of a liquid olefin fraction (8) obtained from said front end deethanizer (3);
   recycling vaporized liquid olefin fraction (11) from said low-temperature separation stage (6) to said gas compressor (1);

removing a hydrogen stream and a methane stream from said low-temperature separation stage (6), and introducing effluent from said low-temperature separation stage (6) to a fractionation stage (7) which separates methane from olefins having two carbon atoms, and removing a methane stream and an olefin stream from said fractionation stage (7) and wherein said method omits a compressor cycle for ethylene refrigerant for said condensation stages.

8. A method according to claim 7, wherein said liquid olefin fraction having two carbon atoms is vaporized via countercurrent flow heat exchangers in said condensation stages.

9. A method according to claim 8, wherein said liquid olefin fraction having two carbon atoms which is vaporized in the countercurrent flow heat exchangers is recirculated to a compressor stage upstream of said front end deethanizer.

* * * * *